United States Patent
Ross et al.

(10) Patent No.: US 11,441,170 B2
(45) Date of Patent: Sep. 13, 2022

(54) COMPOSITIONS, METHODS, AND KITS FOR ONE-STEP DIGESTION OF NUCLEIC ACID FOR ANALYSIS BY LIQUID CHROMATOGRAPHY TANDEM MASS SPECTROMETRY

(71) Applicant: UNIVERSITY OF CINCINNATI, Cincinnati, OH (US)

(72) Inventors: Robert Ross, Erlanger, KY (US); Patrick A. Limbach, Cincinnati, OH (US); Balasubrahmanyam Addepalli, Mason, OH (US); Manasses Jora, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 323 days.

(21) Appl. No.: 16/758,473

(22) PCT Filed: Oct. 26, 2018

(86) PCT No.: PCT/US2018/057696
§ 371 (c)(1),
(2) Date: Apr. 23, 2020

(87) PCT Pub. No.: WO2019/084394
PCT Pub. Date: May 2, 2019

(65) Prior Publication Data
US 2020/0255886 A1    Aug. 13, 2020

Related U.S. Application Data

(60) Provisional application No. 62/577,969, filed on Oct. 27, 2017.

(51) Int. Cl.
*C12Q 1/6806* (2018.01)
*C12N 9/16* (2006.01)
*C12N 9/22* (2006.01)
*C12Q 1/6872* (2018.01)

(52) U.S. Cl.
CPC ............ *C12Q 1/6806* (2013.01); *C12N 9/16* (2013.01); *C12N 9/22* (2013.01); *C12Q 1/6872* (2013.01); *C12Y 301/03001* (2013.01); *C12Y 301/30001* (2013.01); *C12Y 301/31001* (2013.01)

(58) Field of Classification Search
None
See application file for complete search history.

(56) References Cited

FOREIGN PATENT DOCUMENTS

| JP | 2008000043 A | 1/2008 |
|---|---|---|
| WO | 2007067719 A2 | 6/2007 |
| WO | 2017149139 A1 | 9/2017 |

OTHER PUBLICATIONS

Extended European Search Report pertaining to corresponding European Patent Application No. 18869914.4 dated Jul. 7, 2021.
Bendaly, et al., "Differences between human slow N-acetyltransferase 2 alleles in levels of 4-aminobiphenyl-induced DNA adducts and mutations", Mutation Research/Fundamental and Molecular Mechanisms of Mutagenesis, 2009, 13-19, vol. 671 No. 1-2.
Ohira, et al., "Decoding Mechanism of Non-universal Genetic Codes in Loligo bleeker Mitochondria", Journal of Biological Chemistry, 2013, 7645-7652, vol. 288 No. 11.
Quinlivan, et al., "DNA digestion to deoxyribonucleoside: A simplified one-step procedure", Analytical Biochemistry, 2008, 383-385, vol. 373 No. 2.
Krivos, et al., "Removal of 3'-phosphate group by bacterial alkaline phosphatase improves oligonucleotide sequence coverage of RNase digestion products analyzed by collision-induced dissociation mass spectrometry", Rapid Communications in Mass Spectrometry, 2011, 3609-3616, vol. 25, No. 23.
Regal, et al., "Detection and Characterization of DNA Adducts of 3-Methylindole", Chemical Research in Toxicology, 2001, 1014-1024, vol. 14 No. 8.
International Search Report & Written Opinion to corresponding PCT Application No. PCT/US2018/057696 dated Jan. 7, 2019.
Palmgren, et al., "Employment of hydrolytic enzymes in the study of the level of DNA methylation", Biochimica et Biophysica Acta, 1990, 293-297, vol. 1049 No. 3.
Ross, et al., "Sequence mapping of transfer RNA chemical modifications by liquid chromatography tandem mass spectrometry", Methods, 2016, 73-78, vol. 107.
NEB product sheet "Antarctic Phosphatase" Jul. 2013; Retrieved online Dec. 12, 2018.
Robert Ross et al., Sequence mapping of transfer RNA chemical modification by liquid chromatography tandem mass spectrometry, Methods 107 (2016) 73-78.
Gorm Palmgren et al., Employment of hydrolytic enzymes in the study of the level of DNA methylation, Biochimica et Biophysica Acta, 1049 (1990) 293-297.

*Primary Examiner* — Kagnew H Gebreyesus
(74) *Attorney, Agent, or Firm* — Dinsmore & Shohl LLP

(57) ABSTRACT

A kit for preparing a nucleic acid sample for analysis by liquid chromatography tandem mass spectrometry (LC-MS/MS) is provided, the kit comprising: a lyophilized enzyme composition comprising: micrococcal nuclease; nuclease P1; and bacterial alkaline phosphatase (BAP); and a digestion buffer. Also provided are enzyme compositions and methods of use for rapid, efficient preparation of a nucleic acid sample for analysis by LC-MS/MS, without the need for denaturation of the sample.

14 Claims, 2 Drawing Sheets

N'6-methyladenosine     Queuosine     Wybutosine

COMPOSITIONS, METHODS, AND KITS FOR ONE-STEP DIGESTION OF NUCLEIC ACID FOR ANALYSIS BY LIQUID CHROMATOGRAPHY TANDEM MASS SPECTROMETRY

CROSS REFERENCE TO RELATED APPLICATIONS

This application is a § 371 U.S. National Stage Application of International Application No. PCT/US2018/057696 filed Oct. 26, 2018, and claims priority to U.S. Provisional Application No. 62/577,969 filed Oct. 27, 2017, the contents of which are incorporated herein by reference.

STATEMENT REGARDING FEDERALLY SPONSORED RESEARCH OR DEVELOPMENT

This invention was made with government support under R01 GM058843 awarded by National Institutes of Health. The government has certain rights in the invention.

FIELD OF THE INVENTION

The present disclosure relates to compositions, kits, and methods for the preparation of nucleic acid samples for liquid chromatography tandem mass spectrometry (LC-MS/MS).

BACKGROUND OF THE INVENTION

There are over 100 structurally distinct chemical modifications attached to the four canonical RNA nucleosides, adenosine, guanosine, cytosine and uridine. These modifications typically occur post-transcriptionally in the cell and their biological significance is still being unraveled. For example, in human messenger RNA, the modification N,6-methyladenosine, or m6A (FIG. 1), is critical in the degradation of mRNA, where buildup of mRNA transcripts in the cell proves lethal. Geula, S. et al., *A mRNA methylation facilitates resolution of naive pluripotency toward differentiation*, Science 347(6225): 1002-06 (2015). More recently, the same RNA modification was shown to regulate UV-induced DNA damage to cells. Xiang, Y. et al., *RNA m6A methylation regulates the ultraviolet-induced DNA damage response*, Nature 543 (7646): 573-76 (2017). N,6-methyladenosine is just one of over 100 RNA modifications, with multiple biochemical roles; even more are yet to be explored for other nucleoside modifications.

Arguably, the most widespread means of analyzing RNA, either oligomeric or monomeric, is through mass spectrometry. For a monomeric mixture of RNA, the primary mode of characterization is through nucleobase loss from the intact nucleoside. By measuring the mass difference from the base loss, determination of chemical modifications to RNA is possible. Analysis of RNA by mass spectrometry is a mature analytical technique, with over thirty years of method development in bioanalysis. The challenge lies in obtaining the RNA from a sample, then reducing the biopolymer to its individual monomers for analysis. While the mass spectrometric techniques for RNA analysis have improved over the last few decades, the techniques used for preparing RNA for analysis have not.

Long-practiced methods of RNA digestion for mass spectrometric analysis, published almost 25 years ago, remain the primary technique for RNA digestion to nucleosides today. The technique is a three-step process wherein intact RNA is heated to 100 degrees to denature the tertiary structure of the RNA, cooled on ice, then hydrolyzed into oligomers (dimers and trimers) by means of a nuclease enzyme, primarily 3'-5'-Phosphodiesterase (nuclease P1) at acidic pH for two hours at 45° C. The sample is then made basic and a second phosphodiesterase is added and incubated for two hours at 45° C. This digestion takes the small oligomers down to nucleotides, the phosphate containing ribonucleoside, where the phosphate can reside at either the 3' or the 5' position. A third enzyme is then added, which removes the phosphate either at the 3' or 5' position, requiring an additional hour of processing at 37° C. Crain, P. F., Preparation and enzymatic hydrolysis of DNA and RNA for mass spectrometry, Methods Enzymol. 193: 782-90 (1990). Together, the traditional three-step RNA digestion process of Crain requires about 6 hours to prepare a sample for LC-MS/MS.

The standard digestive process is time consuming and includes many steps where pipetting, pH adjustment, and other errors can be introduced. A need exists for a more rapid, streamlined method for digesting nucleic acid for analysis by LC-MS/MS.

SUMMARY OF THE INVENTION

Accordingly, provided herein are compositions, methods, and kits which facilitate complete digestion of total RNA in under four hours, without the need for denaturation, and without the need for multiple pipetting and pH adjustments. The compositions, methods, and kits described herein permit digestion of nucleic acid to its individual nucleoside monomers for LC-MS/MS analysis, by use of a single digestion step composed of a formulation of three digestive enzymes.

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

In one embodiment, a kit for preparing a nucleic acid sample for analysis by liquid chromatography tandem mass spectrometry (LC-MS/MS) is provided, the kit comprising: a container comprising a lyophilized enzyme composition comprising: micrococcal nuclease; nuclease P1; and bacterial alkaline phosphatase (BAP); and a container comprising a digestion buffer.

In another embodiment, an enzyme composition for one-step nucleic acid digestion is provided, comprising: micrococcal nuclease; nuclease P1; and bacterial alkaline phosphatase (BAP).

In another embodiment, a method of preparing a nucleic acid sample for analysis by liquid chromatography tandem mass spectrometry (LC-MS/MS), the method comprising: (a) providing an enzyme composition comprising: micrococcal nuclease; nuclease P1; bacterial alkaline phosphatase (BAP); and a digestion buffer; (b) enzymatically digesting the nucleic acid sample in the enzyme composition to provide a digested nucleoside composition; (c) dehydrating the digested nucleoside composition of step (b) to provide a dehydrated digested nucleoside composition; and (d) rehydrating the dehydrated digested nucleoside composition of step (c) for analysis by LC-MS/MS.

Figure 1:
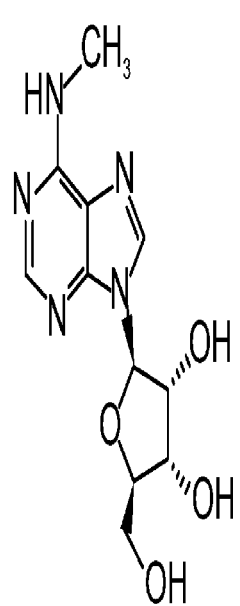
FIG. 1 illustrates the chemical structures of exemplary RNA modifications, m6A, queuosine, and wybutosine.
Figure 1:
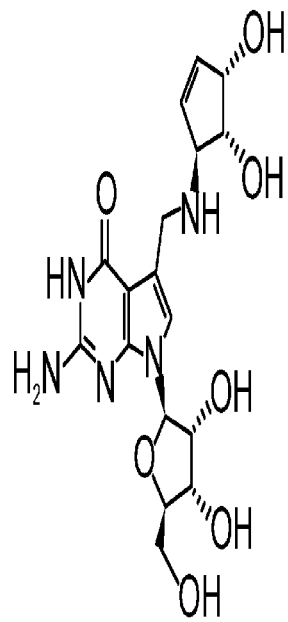
Figure 1:
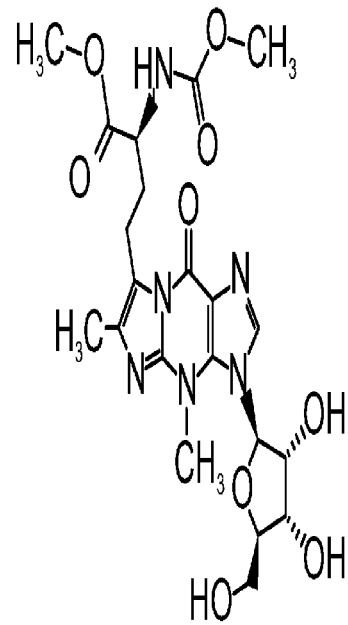

(A) (1) pseudouridine, and (2) uridine;
(B) (1) 3-methylcytidine, (2) 5-methylcytidine, and (3) 2'-O-methylcytidine;
(C) (1) 1-methylpseudouridine, (2) 5-methyluridine, (3) 2'-O-methyluridine;
(D) (1) 1-methyladenosine, (2) 2'-O-methyladenosine, and (3) 6-methyladenosine;
(E) (1) 7-methylguanosine, (2) 2'-O-methylguanosine, and (3) 1-methylguanosine, (4) 2-methylguanosine, and (5) N6-hydroxymethyladenosine;
(F) Queuosine; and
(G) 2-methylthio-N6-isopentenyladenosine.

DETAILED DESCRIPTION

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" or "and combinations thereof" means a combination including at least one of the foregoing elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless otherwise defined, all terms (including technical and scientific terms) used herein have the same meaning as commonly understood by one of ordinary skill in the art to which this disclosure belongs. It will be further understood that terms such as those defined in commonly used dictionaries should be interpreted as having a meaning that is consistent with their meaning in the context of the relevant art and the present disclosure, and will not be interpreted in an idealized or overly formal sense unless expressly so defined herein.

Given the scale of biological research and potential medical role of nucleic acid modifications, there is an urgent need for an efficient, single step nucleic acid digestion kit for LC-MS/MS analysis of post-transcriptional and epigenetic modifications of RNA and DNA. Embodiments described herein provide novel and robust means for digesting nucleic acids down to individual nucleosides, capable of incorporation into automated and high-throughput work flows.

Micrococcal nuclease is an endo-exonuclease that preferentially digests single stranded nucleic acids. Micrococcal nuclease is the extracellular nuclease of *Staphylococcus aureus*, often purified from recombinant *Escherichia coli* cells. Micrococcal nuclease is available for purchase from various vendors, including Millipore Sigma (Miamisburg, Ohio) and Thermo Fisher Scientific (Columbus, Ohio).

Nuclease P1 catalyzes the nonspecific endonucleolytic cleavage of single stranded nucleic acids to yield nucleoside 5'-phosphates and 5'-phosphooligonucleotides. Nuclease P1 is a zinc-dependent endonuclease obtained from *Penicillium citrinum*. Nuclease P1 is available for purchase from various vendors, including MP Biomedicals (Santa Ana, Calif.) and Millipore Sigma (Miamisburg, Ohio).

Bacterial alkaline phosphatase (BAP) is a phosphomonoesterase that hydrolyzes 3' and 5' phosphates from DNA and RNA. BAP is purified from *E. coli* and is available for purchase from various vendors, including Thermo Fisher Scientific (Columbus, Ohio) and Millipore Sigma (Miamisburg, Ohio).

The enzymes disclosed herein are measured in Units, wherein one Unit, or U, is defined by the amount of the enzyme required to transform 1 μmol of substrate per minute.

The term "one-step" or "single step," as used herein, refers to methods of digesting nucleic acid into component nucleosides, wherein the nucleic acid to be digested is added to the enzyme composition and heated at a defined temperature to perform the digestion in a single step. In the single step digestion methods disclosed herein, a separate denaturation step is not required.

"Nucleic acid," as used herein, refers to double-stranded, single-stranded, circular, and linear nucleic acids, either cellular or synthetic. In certain embodiments, the nucleic acid is single-stranded nucleic acid, including RNA and single-stranded DNA. In specific embodiments, the nucleic acid sample for use in the methods disclosed herein is an RNA sample, including a purified RNA sample.

The presently disclosed compositions, kits, and methods permit one-step digestion of nucleic acids into individual nucleosides for use in LC-MS/MS analysis, without the need for a denaturation step. A single step digestion is beneficial in the automation of RNA analysis, where clinical studies may necessitate the need to analyze hundreds of different samples from an investigative cohort. The disclosed nucleic acid digestion compositions, kits, and methods are readily suited to be incorporated into a liquid handling workflow for LC-MS/MS analysis of post-transcriptional modifications of RNA.

Compositions

The compositions suitable for use in the methods and kits disclosed herein for the preparation of nucleic acid samples for analysis by LC-MS/MS comprise a combination of three enzymes: (1) an enzyme that exhibits exo- and endo-phosphodiesterase activities against double-stranded, single-stranded, circular, and/or linear nucleic acids; (2) an enzyme that exhibits endonucleolytic cleavage of single-stranded nucleic acid to yield nucleotides and phosphooligonucleotides; and (3) a non-specific phosphomonoesterase.

Enzymes that exhibit exo- and endo-phosphodiesterase activities against double-stranded, single-stranded, circular, and/or linear nucleic acids include, but are not limited to, micrococcal nuclease, RNase S1, DNase I, DNase II, Benzonase®, phosphodiesterase II, RNase A, RNase H, RNase I, and the like. In a specific embodiment, the enzyme that exhibits exo- and endo-phosphodiesterase activities is micrococcal nuclease.

Enzymes that exhibit endonucleolytic cleavage of single-stranded nucleic acid to yield nucleotides and phosphooligonucleotides include, but are not limited to, nuclease P1, RNase S1, DNase I, DNase II, Benzonase®, phosphodiesterase II, RNase A. RNase T1, RNase I, and the like. In a specific embodiment, the enzyme that exhibits endonucleolytic cleavage is nuclease P1.

Non-specific phosphomonoesterase enzymes include, but are not limited to, bacterial alkaline phosphatase (BAP), Antarctic phosphatase (AP), acid phosphatase, and the like. In a specific embodiment, the phosphomonoesterase enzyme is BAP.

The enzyme compositions are provided as a liquid or lyophilized combination of enzymes.

In embodiments, an enzyme composition for one-step nucleic acid digestion is provided, the composition comprising a combination of enzymes comprising micrococcal nuclease, nuclease P1, and bacterial alkaline phosphatase (BAP).

The selection and quantities of the distinct enzymes will vary, based on the quantity and type of nucleic acid substrate to be hydrolyzed, hydrolysis conditions, reaction time, and the like. For hydrolysis of samples containing up to about 10 μg nucleic acid hydrolyzed at 37° C. for 2 hours, the enzyme composition comprises from about 0.2 to about 1 units micrococcal nuclease; from about 0.05 to about 2 units nuclease P1; and from about 0.0001 to about 0.02 units BAP. In a specific embodiment, for hydrolysis of samples containing up to about 10 μg nucleic acid hydrolyzed at 37° C. for 2 hours, the enzyme composition comprises about 1 unit micrococcal nuclease, about 0.2 units nuclease P1, and about 0.02 units BAP. However, the skilled artisan will appreciate that more or less nucleic acid may be hydrolyzed by adjusting the reaction time, adjusting reaction temperature, and the like. Further, the amounts of the individual enzymes may be scaled to hydrolyze smaller or larger quantities of nucleic acid under the same (i.e., 37° C. for 2 hours) or different reaction conditions. For example, to hydrolyze about 20 μg nucleic acid at 37° C. for 2 hours, the quantity of each enzyme is doubled, i.e., from about 0.4 to about 2 units micrococcal nuclease; from about 0.1 to about 4 units nuclease P1; and from about 0.0002 to about 0.04 units BAP. In a specific embodiment, to hydrolyze about 20 μg nucleic acid at 37° C. for two hours, the composition comprises about 2 units micrococcal nuclease, about 0.4 units nuclease P1, and about 0.02 units BAP. The skilled artisan will appreciate that quantities, reaction conditions, and reaction times may be adjusted as desired to suit individual needs.

In specific embodiments, enzyme composition further comprises a digestion buffer. In embodiments, the digestion buffer comprises zinc (Zn2+) and calcium (Ca2+) ions. Zinc and calcium ions may be provided in various forms, including zinc oxide and calcium chloride, respectively. In embodiments, the zinc oxide is in 5% nitric acid (available as atomic absorption spectrometer standard). In embodiments, the digestion buffer comprises Tris-HCl, Zn2+, and Ca2+. In a specific embodiment, the digestion buffer comprises about 50 mM Tris-HCl at about pH 7.2, about 25 mM Zn2+, and about 5 mM Ca2+.

Methods

In embodiments, a method of preparing a nucleic acid sample for analysis by LC-MS/MS is provided herein, the method comprising: (a) providing a hydrolytic enzyme composition for one-step nucleic acid digestion comprising: (i) an enzyme that exhibits exo- and endo-phosphodiesterase activities against double-stranded, single-stranded, circular, and/or linear nucleic acids; (ii) an enzyme that exhibits endonucleolytic cleavage of single-stranded nucleic acid to yield nucleotides and phosphooligonucleotides; and (iii) a non-specific phosphomonoesterase, and (iv) a digestion buffer; (b) digesting the nucleic acid sample in the hydrolytic enzyme composition to provide a digested nucleoside composition; (c) dehydrating the digested nucleoside composition of step (b) to provide a dehydrated digested nucleoside composition; and (d) rehydrating the dehydrated digested nucleoside composition of step (c) for analysis by LC-MS/MS.

In one embodiment, a method of preparing a nucleic acid sample for analysis by LC-MS/MS is provided herein, the method comprising: (a) providing an enzyme composition for one-step nucleic acid digestion comprising: micrococcal nuclease, nuclease P1, BAP, and a digestion buffer; (b) enzymatically digesting the nucleic acid sample in the enzyme composition to provide a digested nucleoside composition; (c) dehydrating the digested nucleoside composition of step (b) to provide a dehydrated digested nucleoside composition; and (d) rehydrating the dehydrated digested nucleoside composition of step (c) for analysis by LC-MS/MS.

In embodiments, enzymatically digesting the nucleic acid sample in the enzyme composition comprises combining the nucleic acid sample (e.g., a purified RNA sample) with the enzyme composition to form a sample-enzyme mixture; and heating the sample-enzyme mixture to provide a digested nucleoside composition. The skilled artisan will appreciate that various options exist for heating the sample-enzyme mixture, including heating in a water bath or a heat block. In embodiments, the sample-enzyme mixture is heated for about 2 hours at about 37° C.

In some embodiments, dehydrating the digested nucleoside composition comprises lyophilizing or desiccating the digested nucleoside composition. In embodiments, the digested nucleoside composition is dehydrated in a speed vacuum.

After desiccation, the digested nucleoside composition is rehydrated in a suitable solvent. In embodiments, the solvent comprises water or an LC-MS/MS mobile phase solvent. Various mobile phase solvents are known to the skilled artisan and suitable for use in the present methods. In some embodiments, the mobile phase solvent is an ammonium-based buffer solution. In a specific embodiment, the mobile phase solvent is an ammonium-based buffer solution having a molar concentration of about 5 mM and a pH of from about 4.5 to about 5.5.

In an embodiment, the nucleic acid sample comprises up to about 10 µg nucleic acid. Typically, a nucleic acid sample comprising up to about 10 µg nucleic acid may be hydrolyzed using the compositions, kits, and methods disclosed herein in about 2 hours, at 37° C. However, the skilled artisan will appreciate that more or less nucleic acid may be hydrolyzed by adjusting the reaction time, adjusting reaction temperature, and the like. Further, the amounts of the individual enzymes may be scaled to hydrolyze larger or smaller quantities of nucleic acid under the same or different reaction conditions.

In a specific embodiment, in order to hydrolyze up to about 10 µg nucleic in about 2 hours at 37° C., the enzyme composition comprises from about 0.2 to about 1 units micrococcal nuclease; from about 0.05 to about 2 units nuclease P1; and from about 0.0001 to about 0.02 units BAP. In a specific embodiment, for hydrolysis of samples containing up to about 10 µg nucleic acid hydrolyzed at 37° C. for 2 hours, the enzyme composition comprises about 1 unit micrococcal nuclease, about 0.2 units nuclease P1, and about 0.02 units BAP.

In embodiments, the nucleic acid sample is prepared for analysis by LC-MS/MS without the need for a denaturation step.

Kits

In another embodiment, a kit for preparing a nucleic acid sample, e.g., and RNA sample, for analysis by LC-MS/MS is provided, the kit comprising: a container comprising a lyophilized enzyme composition comprising: micrococcal nuclease, nuclease P1, and bacterial alkaline phosphatase (BAP); and a container comprising a digestion buffer. In embodiments, the kit further comprises instructions for preparing the nucleic acid sample for analysis by LC-MS/MS.

In some embodiments, the digestion buffer comprises zinc (Zn2+) and calcium (Ca2+) ions. Zinc and calcium ions may be provided in various forms, including zinc oxide and calcium chloride, respectively. In embodiments, the zinc oxide is in 5% nitric acid (available as atomic absorption spectrometer standard). In embodiments, the digestion buffer comprises Tris-HCl, Zn2+, and Ca2+. In a specific embodiment, the digestion buffer comprises about 50 mM Tris-HCl at about pH 7.2, about 25 mM Zn2+, and about 5 mM Ca2+.

In embodiments, the kit is formulated for preparing a nucleic acid sample comprising up to about 10 µg nucleic acid for analysis by LC-MS/MS. In embodiments, the kit is formulated for preparing up to about 10 µg nucleic acid at about 37° C. for 2 hours. In a specific embodiment, the container comprising a lyophilized enzyme composition comprises: from about 0.2 to about 1 units micrococcal nuclease; from about 0.05 to about 2 units nuclease P1; and from about 0.0001 to about 0.02 units BAP. In another specific embodiment, the container comprising a lyophilized enzyme composition comprises: about 1 unit micrococcal nuclease; about 0.2 units nuclease P1; and about 0.02 units BAP.

EXAMPLES

Specific processes, compositions and kits as described herein are illustrated in the following examples. These examples are provided for illustrative purposes and are not considered limitations on the scope of inventions.

Example 1: Preparation of Human Placenta Total RNA for Analysis by LC-MS/MS

Total transfer RNA (tRNA) was used for the assay as it contains the greatest amount of post-transcriptionally modified nucleosides than any other nucleic acid in the cell. For preparation of a 10 µg sample of total tRNA obtained from human placenta, a lyophilized enzyme composition comprising 1 unit micrococcal nuclease, 0.2 units nuclease P1, and 0.02 units BAP is employed. The enzyme composition is mixed in a tube with 20 µL digestion buffer and gently pipetted to completely resuspend the enzymes. The rehydrated enzyme composition is then added to 10 µg RNA. The tube containing the enzyme-RNA mixture is then heated in a water bath or heat block at 37° C. for 2 hours. The enzyme-RNA mixture is then removed and the contents lyophilized or desiccated in a speed vacuum. The resulting dehydrated digested RNA sample can be stored at 4° C. or rehydrated in mobile phase solvent for use in LC-MS/MS analysis.

Example 2: LC-MS/MS Analysis of Prepared Hydrolyzed RNA

High resolution accurate mass (HRAM) analysis was performed using liquid chromatography tandem mass spectrometry (LC-MS/MS) on a 5 µg injection as described in Ross, R. et al., Sequence mapping of transfer RNA chemical modifications by liquid chromatography tandem mass spectrometry, Methods 107:73-78 (2016).

Figure 2:
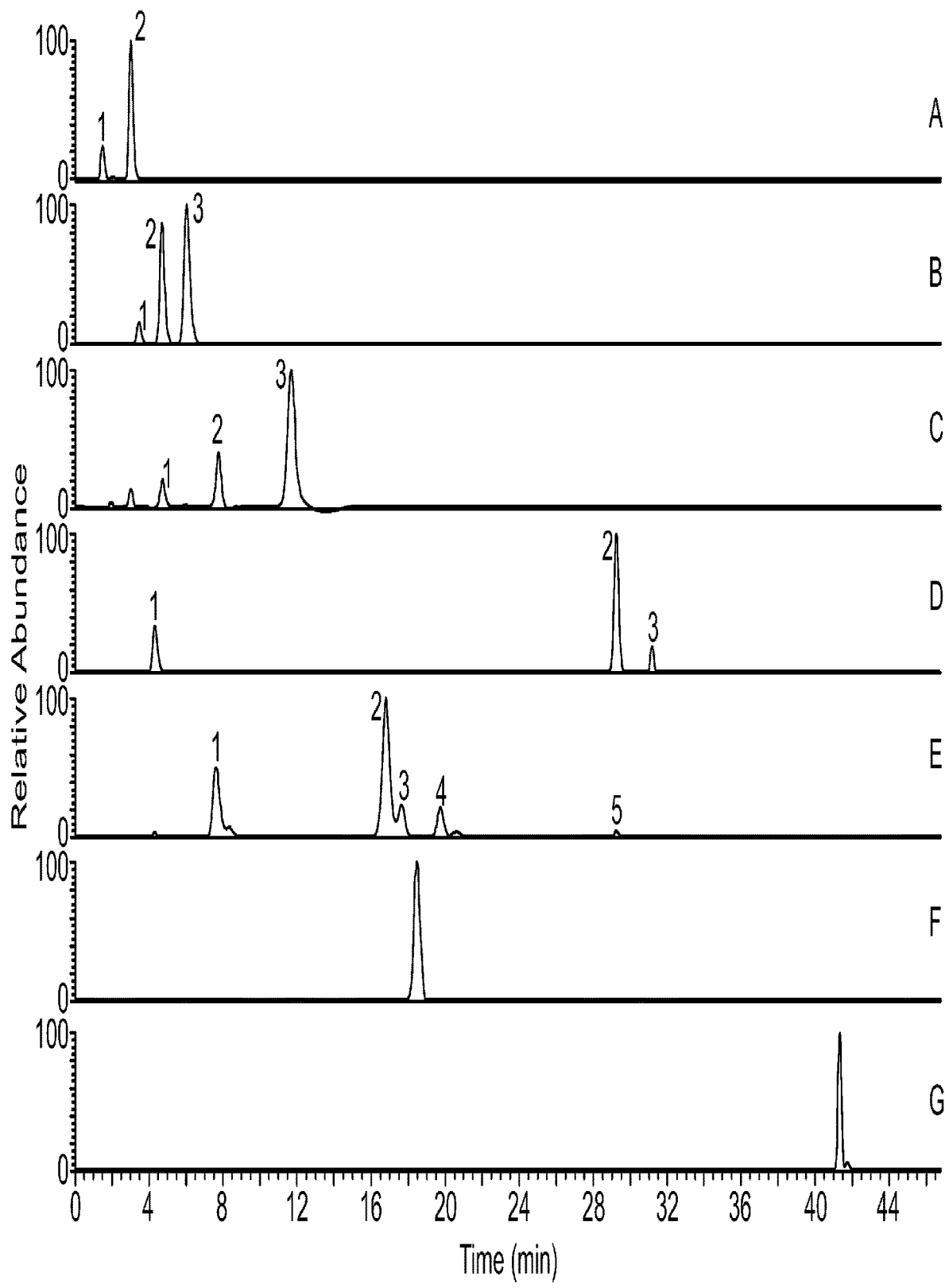
FIG. 2 shows results of high-resolution accurate mass (HRAM) performed using LC-MS/MS analysis of RNA nucleosides from human placenta, prepared using the compositions and methods disclosed herein. Extracted ion chromatograms include.

FIG. 2 shows a representative sample of post-transcriptionally modified nucleosides found in this assay. Extracted ion chromatograms are explained as:

(A) (1) pseudouridine, and (2) uridine;

(B) (1) 3-methylcytidine, (2) 5-methylcytidine, and (3) 2'-O-methylcytidine;

(C) (1) 1-methylpseudouridine, (2) 5-methyluridine, (3) 2'-O-methyluridine;

(D) (1) 1-methyladenosine, (2) 2'-O-methyladenosine, and (3) 6-methyladenosine;

(E) (1) 7-methylguanosine, (2) 2'-O-methylguanosine, and (3) 1-methylguanosine, (4) 2-methylguanosine, and (5) N6-hydroxymethyladenosine;

(F) Queuosine; and (G) 2-methylthio-N6-isopentenyladenosine.

Along with the methylated canonicals, we also detected hypermodified nucleosides such as queuosine (F), which is found solely at one nucleotide position in four tRNAs; and 2-methylthio-N6-isopentenyladenosine. Further, human placenta is known to contain bacterial species. The hypermodified nucleoside 2-methylthio-N6-isopentenyladenosine is not known to exist in humans, however it is known to exist in bacteria. The presence of 2-methylthio-N6-isopentenyladenosine (G) shows that even low abundant RNA species in this assay were digested to their respective nucleosides.

Patents, applications, and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A kit for preparing a nucleic acid sample for analysis by liquid chromatography tandem mass spectrometry (LC-MS/MS), the kit comprising:
a container comprising a lyophilized enzyme composition comprising:
micrococcal nuclease;
nuclease P1; and
bacterial alkaline phosphatase (BAP); and
a container comprising a digestion buffer wherein the digestion buffer comprises about 50 mM Tris-HCl at about pH 7.2, about 25 mM $Zn^{2+}$, and about 5 mM $Ca^{2+}$.

2. The kit of claim 1, wherein the kit is formulated for preparing a nucleic acid sample comprising up to about 10 μg nucleic acid.

3. The kit of claim 2, wherein the container comprising a lyophilized enzyme composition comprises:
from about 0.2 to about 1 units micrococcal nuclease;
from about 0.05 to about 2 units nuclease P1; and
from about 0.0001 to about 0.02 units BAP.

4. The kit of claim 3, wherein the container comprising a lyophilized enzyme composition comprises:
about 1 unit micrococcal nuclease;
about 0.2 units nuclease P1; and
about 0.02 units BAP.

5. A method of preparing a nucleic acid sample for analysis by liquid chromatography tandem mass spectrometry (LC-MS/MS), the method comprising:
(a) providing an enzyme composition comprising:
micrococcal nuclease;
nuclease P1;
bacterial alkaline phosphatase (BAP); and a digestion buffer comprising about 50 mM Tris-HCl at about pH 7.2, about 25 mM $Zn^{2+}$, and about 5 mM $Ca^{2+}$;
(b) enzymatically digesting the nucleic acid sample in the enzyme composition to provide a digested nucleoside composition;
(c) dehydrating the digested nucleoside composition of step (b) to provide a dehydrated digested nucleoside composition; and
(d) rehydrating the dehydrated digested nucleoside composition of step (c) for analysis by LC-MS/MS.

6. The method of claim 5, wherein the enzymatically digesting of step (b) comprises:
combining the nucleic acid sample with the enzyme composition to form a sample-enzyme mixture; and
heating the sample-enzyme mixture to provide the digested nucleoside composition.

7. The method of claim 6, wherein heating the sample-enzyme mixture comprises heating in a water bath or a heat block.

8. The method of claim 5, wherein the dehydrating of step (c) comprises lyophilizing or desiccating the nucleoside composition.

9. The method of claim 5, wherein the rehydrating of step (d) comprises rehydrating in water or an LC-MS/MS mobile phase solvent.

10. The method of claim 9, wherein the LC-MS/MS mobile phase solvent comprises an ammonium-based buffer solution.

11. The method of claim 7, wherein the nucleic acid sample comprises up to about 10 μg nucleic acid and the digesting of step (b) is carried out at about 37° C. for about 2 hours.

12. The method of claim 11, wherein the enzyme composition comprises:
from about 0.2 to about 1 units micrococcal nuclease;
from about 0.05 to about 2 units nuclease P1; and
from about 0.0001 to about 0.02 units BAP.

13. The method of claim 12, wherein the enzyme composition comprises:
about 1 unit micrococcal nuclease;
about 0.2 units nuclease P1; and
about 0.02 units BAP.

14. The method of claim 5, wherein the nucleic acid sample is prepared for analysis by LC-MS/MS without the need for a denaturation step.

* * * * *